(12) United States Patent
Kling et al.

(10) Patent No.: US 6,213,991 B1
(45) Date of Patent: Apr. 10, 2001

(54) ABSORBENT ARTICLE HAVING FASTENER ELEMENTS AND GRIPPING MEANS

(75) Inventors: Robert Kling, Skene; Anna-Karin Jönbrink, Lerum, both of (SE)

(73) Assignee: SCA Hygiene Products AB, Goteborgs (SE)

(*) Notice: Subject to any disclaimer, the term of this patent is extended or adjusted under 35 U.S.C. 154(b) by 0 days.

(21) Appl. No.: 09/194,909

(22) PCT Filed: Apr. 29, 1997

(86) PCT No.: PCT/SE97/00726

§ 371 Date: Jan. 8, 1999

§ 102(e) Date: Jan. 8, 1999

(87) PCT Pub. No.: WO97/46197

PCT Pub. Date: Dec. 11, 1997

(30) Foreign Application Priority Data

Jun. 6, 1996 (SE) .................................... 9602248

(51) Int. Cl.[7] .............................. A61F 13/15; A61F 13/20
(52) U.S. Cl. .................. 604/385.01; 604/396; 604/391; 604/392
(58) Field of Search ..................... 604/385.01, 391, 604/385.4, 389, 390; 24/442, 306

(56) References Cited

U.S. PATENT DOCUMENTS

| | | | |
|---|---|---|---|
| 4,704,107 | * 11/1987 | Coates | 604/357 |
| 4,770,656 | 9/1988 | Proxmire et al. | |
| 5,024,672 | 6/1991 | Widlund | |
| 5,137,526 | * 8/1992 | Coates | 604/391 |
| 5,176,670 | * 1/1993 | Roessler et al. | 604/391 |
| 5,236,429 | 8/1993 | Widlund | |
| 5,370,639 | 12/1994 | Wldlund | |
| 5,399,219 | * 3/1995 | Roessler et al. | 156/259 |
| 5,409,476 | * 4/1995 | Coates | 604/391 |
| 5,707,364 | * 1/1998 | Coates | 604/391 |
| 5,722,127 | * 3/1998 | Coates | 24/304 |
| 5,725,518 | * 3/1998 | Coates | 604/391 |
| 5,814,037 | * 9/1998 | Coates | 604/393 |
| 5,891,122 | * 4/1999 | Coates | 604/385.1 |

FOREIGN PATENT DOCUMENTS

| | | |
|---|---|---|
| 0 215 408 A2 | 3/1987 | (EP) . |
| 0 235 014 | 9/1987 | (EP) . |
| 0 532 034 A2 | 3/1993 | (EP) . |
| 2 297 474 | 8/1996 | (GB) . |
| WO 95/01148 | 1/1995 | (WO) . |

* cited by examiner

Primary Examiner—John G. Weiss
Assistant Examiner—Michele Kidwell
(74) Attorney, Agent, or Firm—Burns, Doane, Swecker & Mathis, L.L.P.

(57) ABSTRACT

An absorbent article comprising a front part which contacts the wearer's stomach during use; a rear part which contacts the wearer's buttocks during use; a crotch part located between the wearer's thighs and extends between said front and rear article parts; an absorbent body located on the crotch part which is enclosed between a liquid-permeable outer material which lies proximal to wear's body in use, and a liquid-impermeable barrier layer which lies distal from the wearer's body in use; a first and second corner portion in respective from and rear parts of the absorbent article, the first and second corner portions each have an first surface and a second surface which is opposed to the first surface; fastener elements disposed on the first surface of the respective first and second portions; a gripping means provided on the second surface of the corner portions of the rear part of said absorbent article.

21 Claims, 3 Drawing Sheets

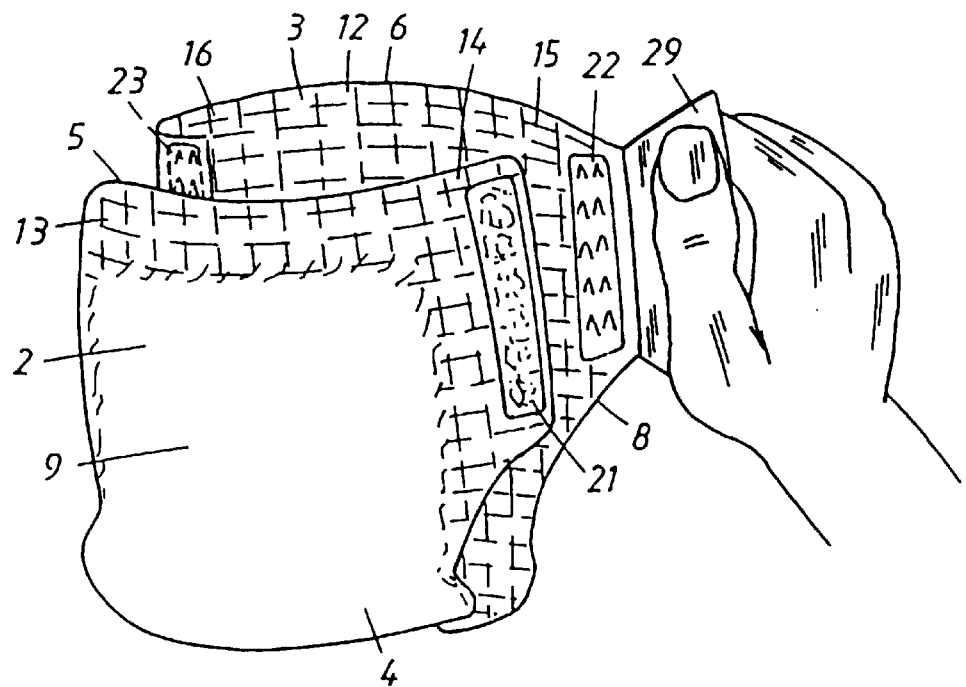
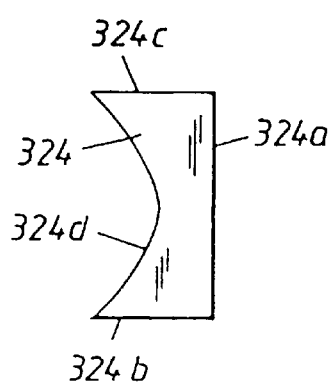 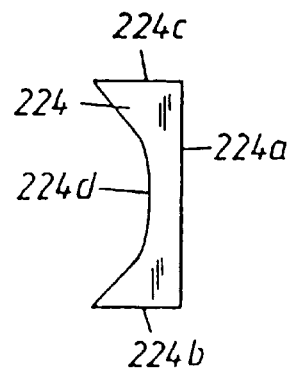 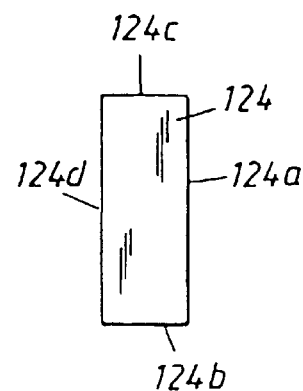

ABSORBENT ARTICLE HAVING FASTENER ELEMENTS AND GRIPPING MEANS

TECHNICAL FIELD

The present invention relates to an absorbent article, such as a diaper, an incontinence guard or like article, having a front part which when the article is worn lies against the stomach of the wearer, a rear part which lies against the buttocks of the wearer and which includes at least one elastic part, and a crotch part which when the article is worn is located between the wearer's thighs and extends between said front and said rear parts, said article extending longitudinally from the rear part to the front part and includes an absorbent body enclosed between liquid-permeable casing material which is intended to lie proximal to the wearer's body in use, and a liquid-impermeable barrier layer which lies distal from the wearer in use, wherein respective front and rear parts of the article have first and second corner portions, each of which has an inner side which is intended to face towards the wearer's body in use, and an outer side which is intended to face away from the wearer's body in use, and longitudinally extending fastener devices disposed in respective corner parts, and wherein the fastener devices in respective corner parts of said rear part are disposed on the inside of respective corner parts.

By diaper is meant preferably disposable diapers and openable and re-closable pant diapers and by incontinence guard is meant diapers intended primarily for older children or for adults.

DESCRIPTION OF THE BACKGROUND ART

Absorbent articles, such as diapers for children and adults, have long been provided with fastener devices by means of which, e.g., a parent is able to fasten together respective corner parts of the front and rear diaper parts, such that the diaper will sit around the wearer's abdomen in a pants-like fashion. These fastener devices can subsequently be released to permit removal of the diaper after use. Examples of such fastener devices are adhesive coatings and mechanical locking devices. These latter devices may have the form of press studs, buttons and button holes, so-called touch and close fasteners (i.e. fasteners comprising hook and loop fastener elements). Both the adhesive and mechanical fasteners may be mounted on fastener tabs attached to the article, conveniently in the vicinity of the two corner portions of the rear part of the diaper.

Examples of diapers provided with such adhesive fastener tabs are described in Swedish Patent Specification 446 056. The diaper according to SE 446 056 is also provided with one or more plastic strips attached along the end edge of the diaper and extending from corner to corner on the front part of the diaper. When using the diaper, the plastic strip or strips functions/function as an attachment surface for fastening of the fastener tabs. The plastic strip is of a nature which will allow the fastener tabs to be released therefrom without detriment either to the adhesive coating on the tabs or to the plastic strip. This enables the fastener tabs to be refastened to the plastic strip, e.g. after a parent has inspected the diaper to ascertain whether or not the diaper needs to be changed and has not found this to be the case.

It is known to use mechanical fastener devices as diaper fastener means as an alternative to adhesive fastener means. European Patent Specification EP 0 235 014 B1 is an example of the patent literature relating to diapers provided with mechanical fastener tabs. The fastener system described in this specification is similar in many respects to the system illustrated in SE 446 056, but with the difference, of course, that the fastener means are mechanical, more specifically of the touch and close type.

It is also known to attach fastener devices directly to the inside or the outside of the diaper casing, i.e. in the total absence of fastener tabs.

The fastener systems of the kind described in SE 446 056 and EP 0 235 014 B1 also include fastener tabs which are elongated in the transverse direction of the diaper and which are substantially narrower than the distance between the end edge of the diaper at the diaper waist opening and respective diaper leg openings. These fastener tabs are normally less than 25 mm in width. On the other hand, EP 0 215 408 for instance describes fastener devices which are mounted directly on the diaper casing essentially in the longitudinal direction of the diaper and which extend fully from the diaper waist opening to respective diaper leg openings.

The diaper illustrated in EP 0 215 408-1 also has an elastic outer casing which can be stretched and allowed to contract around the wearer's body.

SE 9500386-9 (filing date Feb. 2nd, 1995) describes an absorbent pant diaper that includes an elastic pants-type sheet or layer which fits tightly against the wearer's body, whereas the outer casing sheet and the absorbent body are essentially unaffected by forces stemming from the pants-type layer.

Diapers will normally have elastic rear and front parts, sometimes limited to certain zones of said parts, for instance along the end-edges or in the corner portions of the front and/or rear parts of the diaper. The purpose of making the whole or parts of the front and rear parts of the diaper elastic is to enable the diaper to sit tightly around the waist of the wearer. This so-called waist elastic is intended to hold the diaper tightly against the wearer's body so that no urine will leak through the diaper waist opening, and also to keep the diaper in position on the wearer's body when the diaper has absorbed liquid to an extent which causes the diaper to sag.

One of the most usual methods of applying a diaper provided with the aforesaid types of fastener devices is to place the diaper carrier (e.g. a baby) on its back and to pass the rear part of the diaper beneath the baby's bottom and then past the part of the diaper between the legs and up over the baby's stomach. The front and rear diaper parts are then mutually secured by means of the fastener devices.

Absorbent articles that include elastic rear parts, primarily such articles that include relatively strong elastic, often exhibit relatively heavily contracted rear parts when no load acts on the diaper. This is because the rear part of the diaper, and primarily its rear corner portions, generally consist solely of relatively pliable casing material, such as non-woven material and polyethylene film.

As a result of this heavy or pronounced contraction, a parent attempting to put a diaper on a baby with the baby lying on its back, ie in a so-called recumbent position, may find it difficult to grip the corners of the diaper, because the rear diaper part has contracted elastically to such an extent as to draw the corners inwardly beneath the baby's bottom or backside.

With regard to diapers provided with fastener tabs, it is feasible in theory that the corners could be gripped more readily if the corners were larger in size, since this would enable the fastener tabs to be used as "handgrips". However, in the packaged state of the diaper, fastener tabs are normally folded in over the diaper casing material and releasably fixed thereto. When the fastener means is an adhesive, fastener tabs may be fastened to a release layer or film on the casing material or to a region of the casing material that has been treated with a release agent. Fastener tabs provided with mechanical fastener elements are also normally folded in over the diaper casing material in a corresponding manner.

In order to avoid the adhesive coming into contact with the wearer's skin, the fastener tabs are not released until they are to be fastened to the front part of the diaper. If the fastener tabs are released prematurely, the risk of the fastener means coming into contact with the wearer's skin is extremely great in the case of diapers whose rear parts are heavily contracted by elastic devices, since, as before mentioned, the corners of such diapers will be located beneath the wearer's body when the wearer lies on his/her back. Consequently, it is not possible in practice to use the fastener tabs as a form of grip in order to obtain better purchase when the corner parts of the diaper lie beneath the wearer and cannot readily be reached.

When the fastener means has the form of mechanical fastener elements, for instance touch and close fasteners, instead of an adhesive, there is a corresponding desire to prevent the wearer's skin becoming marked by said fastener means, and consequently such fastener tabs are equally as unsuitable for use as gripping means as the adhesive fastener tabs under corresponding conditions.

The use of fastener tabs with diapers that include relatively large elastic regions in the front and/or rear parts of the diaper also leads to another drawback. A fastener tab is normally relatively non-elastic and has its largest extension in the waist region of the diaper. Consequently, the fastener tab occupies a not inconsiderable portion of the front diaper part when fixed thereto, thereby impairing the elasticity of said front part. Naturally, that portion of the fastener tab which in manufacture is permanently attached to the respective corner portions of the rear diaper part will also occupy a not inconsiderable portion of the rear diaper part, thereby preventing this portion being used to apply elastic forces to the diaper with the intention of keeping the diaper in place on the wearer. In other words, a smaller part of the waist region of the diaper can be used to generate diaper holding elastic forces when the diaper is provided with transversely extending fastener tabs that when such tabs are not included.

Those diapers with which fastener devices are mounted directly on the diaper casing, similar to the diaper according to EP 0 215 408 B1, have other drawbacks. Since such devices need to be relatively long in order to extend from the edge of the waist opening to respective leg openings, they are also longer than the normal finger breadth of a human hand. Consequently, such devices are difficult to apply to their corresponding fastener devices (which are equally as long) in the corners of the front diaper part with the same grip as that taken on the fastener device in order to stretch the elastic in those parts of the diaper extending around the waist region. The fingers used to secure the fastener devices are also liable to become positioned between those fastener devices that are to be mutually secured, which is undesirable of course.

OBJECTS AND MAIN CHARACTERISTIC FEATURES OF THE INVENTION

One object of the present invention is to solve the aforesaid problems encountered with known fastener devices.

It is also a particular object of the present invention to provide an absorbent article, such as a diaper, which facilitates a diaper change when the diaper includes relatively strong elastic in the front and/or rear parts of the diaper.

This object is achieved with an absorbent article of the kind defined in the introduction which is characterized by gripping devices disposed on the outside of the corner portions of the rear diaper part.

The present invention provides an absorbent article whose fastener devices are disposed so as to enable the largest possible areas of the front and rear parts of the article to be used for active waist elastic. The invention also provides means which enables the corner parts of the diaper to be gripped more easily and drawn from their position beneath the wearer, when the wearer lies on his/her back. The invention also provides a handgrip with the aid of which relatively long fastener devices seen in the longitudinal direction of the article can be secured or connected with the use of several fingers at the same time, without any part of the hand being located between the fastener devices.

In one preferred embodiment of the invention, the gripping means comprises a pocket, flap, loop or like device connected to the outside of the corner portion.

According to one variant, the gripping means is comprised of a part of the corner portion that is folded over itself in the transverse direction of the article, said folded part being joined to the outer surface of the remaining part of the corner portion along their transverse edges so as to form a pocket.

According to one preferred embodiment of the invention, the gripping means is elongated and has a longitudinal side-edge which extends generally parallel with that edge of respective corner portions that extends generally in the longitudinal direction of the article, two transverse end edges which are orientated generally in the transverse direction of the article, and a curved longitudinal side edge, wherein the gripping means is joined to the corner portion along at least one of its edges.

In another embodiment of the invention, the gripping means is generally rectangular and elongated and one of its longest sides extends generally parallel with that edge of a respective corner portion which extends generally in the longitudinal direction of the article, wherein the gripping means is joined to said corner portion along at least one of its edges.

According to one particularly preferred embodiment of the invention, the gripping means is joined to the corner portion along two or three of its edges, wherein the free edge is that edge of the gripping means which is located nearest a longitudinally extending contemplated article centre line. In this way, the gripping means has the form of a loop and a pocket on the outside of respective corner portions. These embodiments have the advantage that the gripping means need not be manipulated by the person handling the diaper, e.g. unfolded from a position between the diaper carrier and the liquid-permeable casing material of the diaper, as is necessary in the case of a fastener tab according to the aforesaid known patents, but is immediately available for use on the side of the corner portion opposite the fastener device.

According to another preferred embodiment of the invention, the gripping means is joined along one single edge, edge-to-edge, with the side edge of a respective corner portion that extends generally in the longitudinal direction of the article from the waist end edge to the crotch part.

According to one particularly preferred variant of the embodiment defined in the preceding paragraph, additional fastener means are arranged on the gripping means, these additional fastener means being intended to provide a releasable and refastenable connection with the outer surface of the corner portion, thereby enabling the gripping means to be released from the outside of said corner portion and thereafter used when closing the fastener means on the front corner portions of the article with fastener means on the rear corner portions of said article such as to form a pants-type garment having a waist opening and two leg openings, whereafter the gripping means can again be connected to the outside of respective rear corner portions by means of the additional fastener means.

Although this embodiment involves manipulating the gripping means before it is used, it has the advantage of enabling the corner portions of the diaper to be extended by first releasing the connection between the additional fastener means and the outside of the corner portions and then unfolding the gripping means, i.e. the grip flaps, such that the grip flaps extend further out from one side of a recumbent wearer and, in the best of cases, will be fully visible and reachable from one side of the wearer, depending on the size and stature of the wearer, the size and shape of the grip flaps and the extent to which contraction of the rear part is affected by the elastic. After securing together the front and rear parts of the diaper, the grip flaps are again affixed to the outside of the corner portion by means of the additional fastener means, so that said grip flaps are not left hanging to flap about.

According to another advantageous embodiment of the invention, respective grips are disposed generally opposite respective fastener means in its position of use.

This provides a convenient press application angle, namely along the normal to the plane of the fastener means, when gripping the gripping means and joining the fastener means together when putting on the diaper. In the case of the aforedescribed embodiment in which the gripping means is connected along only one single edge, the gripping means is folded back in over the outside of the corner portion of the article at the moment of joining the fastener means together, whereafter the fingers of the person applying the diaper are guided in towards a position generally immediately above the fastener means that are to be joined together. This feature is described in more detail with reference to the following description of preferred embodiments.

According to a further advantageous embodiment of the invention, the extension of the gripping means in the longitudinal direction of the article is at least equal to the extension of the fastener means in the longitudinal direction of the article in respective corner portions. This enables pressure to be applied over the entire surface of the fastener means at the moment of connection, and not solely to those parts of the fastener means to which one would have been restricted if the surface of the layer had been smaller than the total surface area of the fastener means. It can be mentioned in this respect that each corner portion may include several fastener means, and hence it is the total surface area of these fastener means that is related to the surface area of the layer or sheet.

It will be understood that the present invention also provides a diaper which can be applied to an upstanding diaper carrier in an advantageous manner, even though some of the aforesaid advantages are particularly related to problems that arise when applying a diaper to a recumbent wearer.

BRIEF DESCRIPTION OF THE DRAWINGS

The invention will now be described with reference to exemplifying embodiments thereof and also with reference to the accompanying drawings, in which

FIG. 7 is a perspective view of the diaper shown in FIG. 4 and illustrates schematically the manner in which the invention is intended to be applied when putting on the diaper; and FIG. 8 illustrates a number of alternative embodiments of the inventive gripping means.

DESCRIPTION OF EXEMPLIFYING EMBODIMENTS

Figure 1:
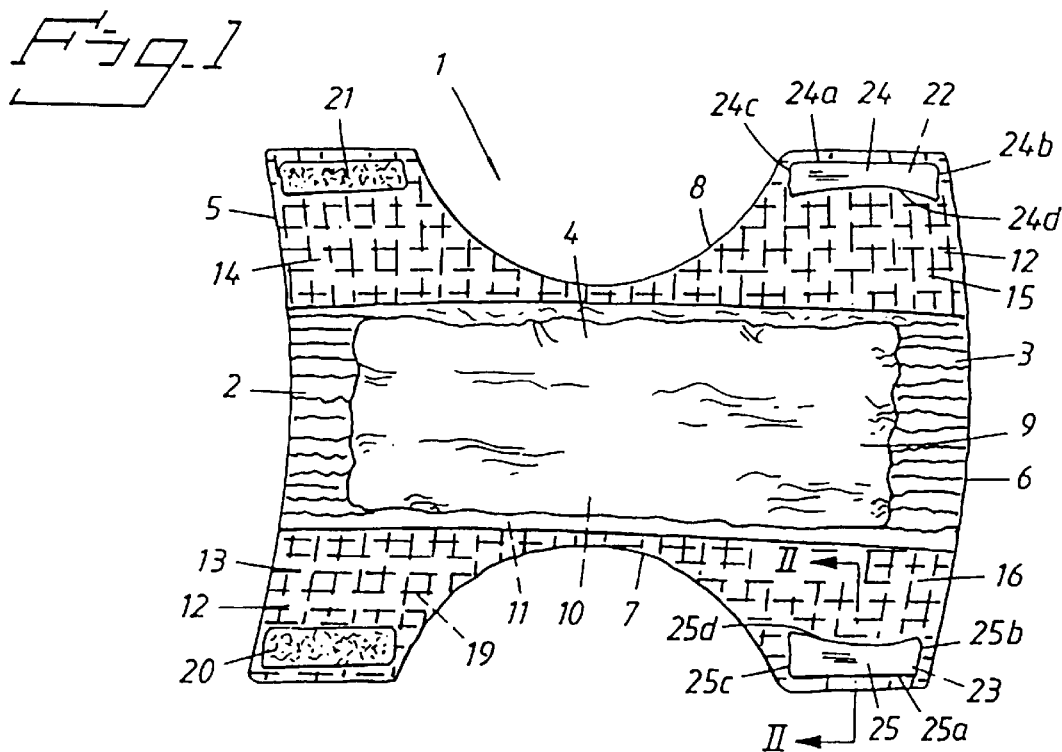
FIG. 1 illustrates from above a diaper according to a first embodiment of the invention.
Figure 3:
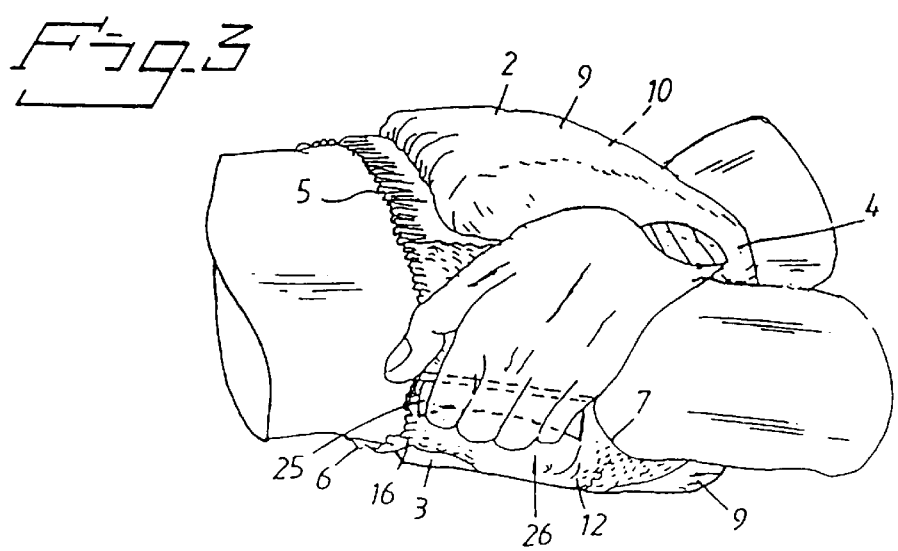
FIG. 3 is a perspective view of the diaper shown in FIG. 1 and illustrates schematically the manner in which the invention is intended to be applied when putting on the diaper.

FIG. 1 illustrates a diaper 1 according to a first embodiment of the invention. The diaper 1 is shown in FIG. 1 with that side of the diaper which is intended to lie distal from the wearer's body in use faces towards the viewer. The diaper 1 has a front part 2 which is intended to lie against the stomach of the wearer when the article is worn, a rear part 3 which is intended to lie against the wearer's bottom when the article is in use, and a crotch part 4 which is located between the front and the rear parts of the article and which is intended to be placed between the wearer's legs. The positions of the various parts in relation to the wearer's body are also shown in FIG. 3.

The diaper 1 thus has a front end-edge 5, a rear end-edge 6 and two side-edges 7, 8. The two side-edges 7, 8 curve towards one another in the crotch part 4, so that the crotch part 4 is narrower than the front part 2 and the rear part 3. When the diaper is placed on the wearer, these parts of the side-edges 7, 8 will embrace the wearer's legs and thus form the edges of leg openings. Correspondingly, the end-edges 5, 6 will together embrace the wearer's stomach and back and therewith form a waist opening (see FIG. 3). In the state of the article shown in FIG. 1, the distance from the rear end-edge 6 to the front end-edge 5 is greater than the distance between the side-edges 7, 8 and is consequently designated the direction from the rear end-edge 6 to the front end-edge 5 in the longitudinal direction of the diaper. The diaper also has a contemplated longitudinally extending center line positioned symmetrically between the two side-edges 7,8.

The expression "essentially in the longitudinal direction of the article" includes by definition every direction which deviates from the longitudinal direction of the article by an acute angle that is smaller than or equal to 45°. By the expression "essentially in the transverse direction of the article" includes by definition every direction which deviates from the longitudinal direction of the article by an acute angle which is greater than 45°.

The diaper 1 also includes a liquid-impermeable barrier layer 9, for instance a polyethylene layer, an absorbent body 10 located inwardly of said barrier layer, and liquid-permeable outer material 11 located on the other side of said absorbent body 10. The absorbent body 10 and the outer material 11 are located behind the barrier layer 9 in the FIG. 1 illustration and cannot therefore be seen in FIG. 1. The outer material 11 and the barrier layer 9 have an essentially rectangular surface and essentially mutually the same shape and size. The absorbent body 10 is smaller than the outer material 11 and the barrier layer 9 in all directions and is enclosed therebetween. The outer material 11 and the barrier layer 9 may be joined together by conventional techniques, such as gluing, for instance. The absorbent body may also be joined to the outer material and/or the barrier layer, for instance by gluing. The outer material 11 may be any type of known liquid-permeable material, such as nonwoven material, e.g. a spun-bonded or thermobonded material. The absorbent body 10 may also comprise any conventional absorbent material, such as fluff pulp of chemical or chemithermomechanical type. Naturally, the absorbent body may also contain absorbent gel-forming polymers, absorbent foam material, etc.

The diaper 1 also includes a so-called elastic pants layer 12 which is located inwardly of the outer material 11 (i.e. closer to the wearer's body) and extends transversely of the diaper outwardly of the side edges of the outer material 11 and the barrier layer 9, such as to form four corner portions 13–16 in respective front and rear parts 2, 3 of the diaper. When the diaper is worn (see FIG. 3), the elastic pants layer 12 will lie against the wearer's body. The elastic pants layer 12 is comprised of an inner nonwoven material 17 and an outer nonwoven material 18, both being for instance spun-bonded material, having sandwiched therebetween an elastic net 19 which is elastic in both the longitudinal and the transverse direction of the diaper. The elastic forces are preferably active essentially transversely of the diaper in the rear and front parts 3, 2 thereof respectively, and generally in the crotch part 4 of the diaper longitudinally thereof. Naturally, it is conceivable for the elastic pants layer to be made of some other material, for instance other types of nonwoven material than spun-bonded, elastic film, elastic nonwoven material, elastic threads, etc.

The elastic pants layer 12 may be of the kind described in our Swedish Patent Application SE 9500386-9 (filing date Feb. 2nd 1995). Such a pants layer is provided with one or more openings through which urine and/or faeces can pass. The pants layer 12 is stretch-connected to the outer material 11 and to the barrier layer 9 solely in the peripheral regions thereof, so that the pants layer 12 is able to contract and drawn out without being affected by forces emanating from the barrier layer 9 to any great extent, therewith enabling the pants layer 12 to lie against the wearer's body essentially over the whole of its surface with no gaps between the pants layer 12 and the wearer's body. The absorbent body 10 will therewith be located at a relatively large distance from the pants layer 12 when the diaper is worn. The reader is referred to SE 9500386-9 for a more detailed description of the elastic pants layer.

It will be understood that the invention is not restricted to the elastic pants layer 12 disclosed in SE 9500386-9, and that the pants layer can be connected conventionally to the outer material 11 across the whole of the surface of said material or across parts thereof. Alternatively, it is feasible that those parts of the elastic pants layer 12 shown in FIG. 1 that extend laterally outside the barrier layer 9 may comprise two separate layers which have been joined between the side-edge parts of the outer material and the barrier layer on respective long sides of the absorbent body 10. In this case, the outer material 11 will also lie against the wearer's body and not only the pants layer 12. Another alternative is for the outer material and the barrier layer to be given an extension and shape such that their edges will also form the end edges and side edges 5–8 of the diaper, in a well-known manner. In this case, the corner portions of the diaper will include parts of the outer material and the barrier layer between which elastic devices may have been mounted. The elastic pants layer can be omitted in this case. Naturally, it is also feasible to provide elastic devices between barrier layer and outer material in those regions thereof that extend beyond the end edges and side edges of the absorbent body in regions of the diaper other than in its corner portions, for instance along the diaper end edge regions, i.e. that region of the diaper which forms a waist part when the diaper is worn.

Figure 2:
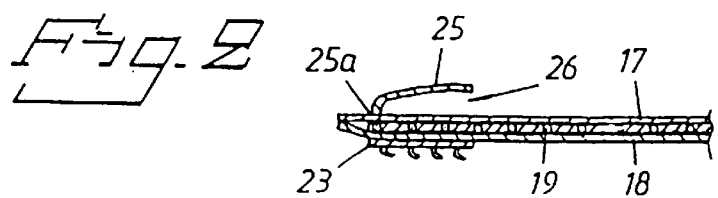
FIG. 2 is a cross-sectional view taken on the line II-II in FIG. 1 and shows gripping means in accordance with the first embodiment of the invention.

Four fastener devices 20–23 are mounted in the four corner portions 13–16. The fastener devices 20–23 are mechanical devices, more specifically hook & loop type fastener devices. The fastener elements 20, 21 provided in the corner portions 13, 14 of the front part 2 of the diaper are comprised of velour or some other material that includes a plurality of loops or the like with which hook-carrying fastener elements 22, 23 in the corner portions 15, 16 of the rear diaper part 3 can fasten. The hook-carrying fastener elements 22, 23 of the FIG. 1 embodiment are located on the underside, i.e. the inside, of respective corner portions 15, 16 and therefore cannot be seen in the FIG. 1 illustration. FIG. 2, on the other hand, shows the placement of the hook-carrying element 23. FIG. 2 shows four hooks protruding from a substrate layer, these hooks together illustrating the hook-carrying element 23 of the hook and loop fastener. Naturally, the hooks may have any desired shape and be present in any desired number, and the form illustrated need not necessarily coincide with the appearance of the actual fastener element used, and hence FIG. 2 shall be seen merely as an illustrated example.

As will be understood, the fastener devices 20–23 may be comprised of other mechanical fastener elements, such as buttons and buttonholes, hooks and eyes, press studs, preferably vacuum-formed press studs, different extruded profile shapes, and so on. Naturally, the positioning of the loop-carrying and the hook-carrying fastener devices may be reversed, such that the hook-carrying elements are instead placed on the front part of the diaper and the loop-carrying elements on the rear part thereof. The fastener elements may also be placed crosswise, such that one hook-carrying element is located in one of the corner portions of the front diaper part and one element in a diametrically opposed corner portion of the rear diaper part. Naturally, the loop-carrying elements will be positioned correspondingly, although in the two remaining corner portions. This and other arrangements are described in more detail in our Swedish Patent Application SE 9502492-3, to which the reader is referred.

Naturally, adhesive fastener devices or cohesive binders can be used, i.e. binders which will only fasten to themselves. The number of fastener devices used in respective corner portions may also be more than the single fastener device shown in FIG. 1, irrespective of whether the devices are adhesive, cohesive, mechanical or have some other form. For instance, the single elongated fastener element 22, 23 may be replaced with a row of several shorter fastener elements which together have the same extension as the fastener element shown in respective corner portions in FIG. 1. The two fastener elements 20, 21 in the front diaper part 2 may alternatively be replaced with a single fastener element which extends transversely of the diaper along the front end-edge 5 thereof in the manner shown from EP 0 235 014 B1 and SE 446 056.

Gripping means 24, 25 are provided in the corner portions 15, 16 of the rear diaper part 3 on the opposite side of the pants layer 12 to the fastener elements 22, 23. The gripping means 24, 25 may be comprised of a layer or a flap of suitable grip-friendly material, for instance a nonwoven material or plastic film. The gripping means 24, 25 are elongated in the longitudinal direction of the diaper and extend essentially fully from the center edge 6 to that part of respective side-edges 7, 8 which is curved to form respective leg openings. Should this edge extension be cut obliquely or angled in some other way from the longitudinal axis of the diaper, the gripping means will nevertheless be considered to be elongated in the direction of the long axis of the diaper in this document, provided that their longest side is angled at a maximum of 45° in relation to the longitudinal axis of the diaper. Since the edge 24d, 25d located nearest the contemplated longitudinal center line is curved, the aforesaid definition is considered to apply for the longest linear part of the longest edge. If the entire edge is non-linear, the tangent to the edge curve shall exhibit at most an angle of 45° to the longitudinal axis of the diaper over more than 50% of the length of the edge between said leg opening and said waist edge.

The gripping means 24, 25 are disposed essentially opposite their respective fastener elements 22, 23 and have essentially the same size and shape as these elements. Respective gripping means 24, 25 are also joined to the pants layer 12 along three of their edges 24a–c, 25a–e, i.e. all edges with the exception of the edge 24d, 25d which lie closest to the longitudinally extending contemplated diaper center line. This edge 24d, 25d is thus not joined to the underlying pants layer 12, whereby the whole of the gripping means 24, 25 constitutes a sort of pocket 26 (see FIGS. 2 and 3) into which the user can insert his/her fingers and grip the gripping means 24, 25 and hereby stretch-out the entire pants layer 12 which, in a relaxed state, is drawn together or puckered, as will best be seen from FIG. 3.

The purpose of the gripping means 24, 25 is to enable the diaper 1 provided with elastic front and rear parts 2, 3 to be placed more easily on a wearer. When applying the diaper to a recumbent user, the rear corner portions 15, 16 of the diaper will typically be so contracted as to lie relatively inaccessible beneath the diaper wearer. If no gripping means 24, 25 were provided, the person involved in handling the diaper would need to insert his/her hands beneath the wearer and grip a respective corner portion 15, 16 with the fingers placed on opposite sides of the pants layer 12. Firstly, it is difficult to localize the corner portions of the diaper when these portions are hidden beneath the wearer. Secondly, it is difficult to grip a thin, highly pliable layer of material, such as the pants layer 12, and stretch the layer out flat before fastening the fastener elements of the fastener device, at which time it is necessary to grip the pants layer 12 with the fingers on opposite sides of said layer, wherewith said person has four fingers on one side of the layer and solely the thumb as a counterpressure means on the other. Thirdly, the thumb will be in the way when fastening together the respective fastener elements 20, 23 and 21, 22.

FIG. 3 illustrates schematically a hand of a person handling the diaper, with the person's fingers inserted in the pocket 26 between the gripping means 25 (indicated in broken lines) and the pants layer 12. The person handling the diaper has just terminated the task of securing the two fastener elements 20, 23, which lie hidden on the inside of the pants layer 12 opposite the gripping means 25.

The inventive diaper 1 is applied by gripping the gripping means 25 (see FIG. 3) with an appropriate number of fingers, for instance four fingers inserted into the formed pocket 26. It is found that the curved free edge 25d greatly facilitates insertion of the fingers into the pocket 26, as opposed to a straight edge. The person handling the diaper then pulls on the gripping means 25, therewith extending the elastic pants layer 12, and therewith also the rear diaper part 3, from its elastic, non-loaded state to an elastically stretched state. The aforesaid person then places the hook-carrying element 23 against the loop-carrying element 20, which may possibly be moved into position with the aid of the other hand. Because of the configuration of the grip flap, the fastener elements 20 and 23 can then be pressed together and secured with the fingers of said person inserted into the pocket 26 (more specifically those parts of the fingers that extend up to the outermost knuckles or finger joints), without the thumb being obstructed and without said person needing to change his/her grip.

This procedure is much more advantageous from a gripping and pulling aspect than when the pants layer 12 is "nipped" directly between the finger tips and the fingers pressed together from opposite sides of the layer, when it is necessary to stretch the elastic devices provided in the rear part of the diaper.

FIG. 3 illustrates a recumbent diaper carrier, although it would be understood that the gripping means 25 is handled principly in a similar manner when placing a diaper on an upstanding carrier.

The gripping means 24, 25 are preferably welded to the pants layer 12, e.g. by ultrasonic welding, although the flaps may be joined to said layer by gluing, heat-sealing or some other conventional technique. In one variant, the gripping means are comprised of a part of the corner portion which is folded over itself in the transverse direction of the article, said folded-over part being connected to the outside of the remaining parts of the corner portion along their transverse edges so as to form a pocket.

FIG. 8 illustrates alternative embodiments of gripping means according to the embodiment shown in FIGS. 1–3. These gripping means are referenced 24 and their edges are referenced 24a–d preceded by a 1, a 2 and a 3 respectively. The gripping means 124 are essentially rectangular in shape. The gripping means 224 has a free opening edge 224d having a slightly larger radius of curvature and thus a pocket of slightly shallower depth than the corresponding opening edge 24d in FIG. 1. The gripping means 324 has slightly longer short sides 324b–c than the remaining gripping means in FIG. 1 and FIG. 8. It will be readily understood that the geometric shape of the gripping means can be varied in other ways.

In an alternative embodiment of the invention which has not been shown explicitly in the Figures but which nevertheless can be readily described with reference to FIG. 1, the gripping means 24, 25 are connected only along their two end-edges 24b, 24c and 25b, 25c respectively. Instead of a pocket this will result in a loop into which the fingers can be inserted in principly the same way as fingers can be inserted into the pocket shown in FIGS. 1–3. The fastener devices 20, 23 are, in principle, closed in the same way as that described above with reference to the gripping means 25 shown in FIG. 3.

A second exemplifying enmbodiment of the present invention will now be described with reference to FIGS. 5–7. Structural elements of the same kind as those included in the first embodiment shown in FIGS. 1–3 have been identified in FIGS. 4–7 with the same reference signs as those used in FIGS. 1–3. In order to avoid unnecessary repetition, reference is therefore made to the description of the first embodiment with regard to such common structural elements.

Figure 4:
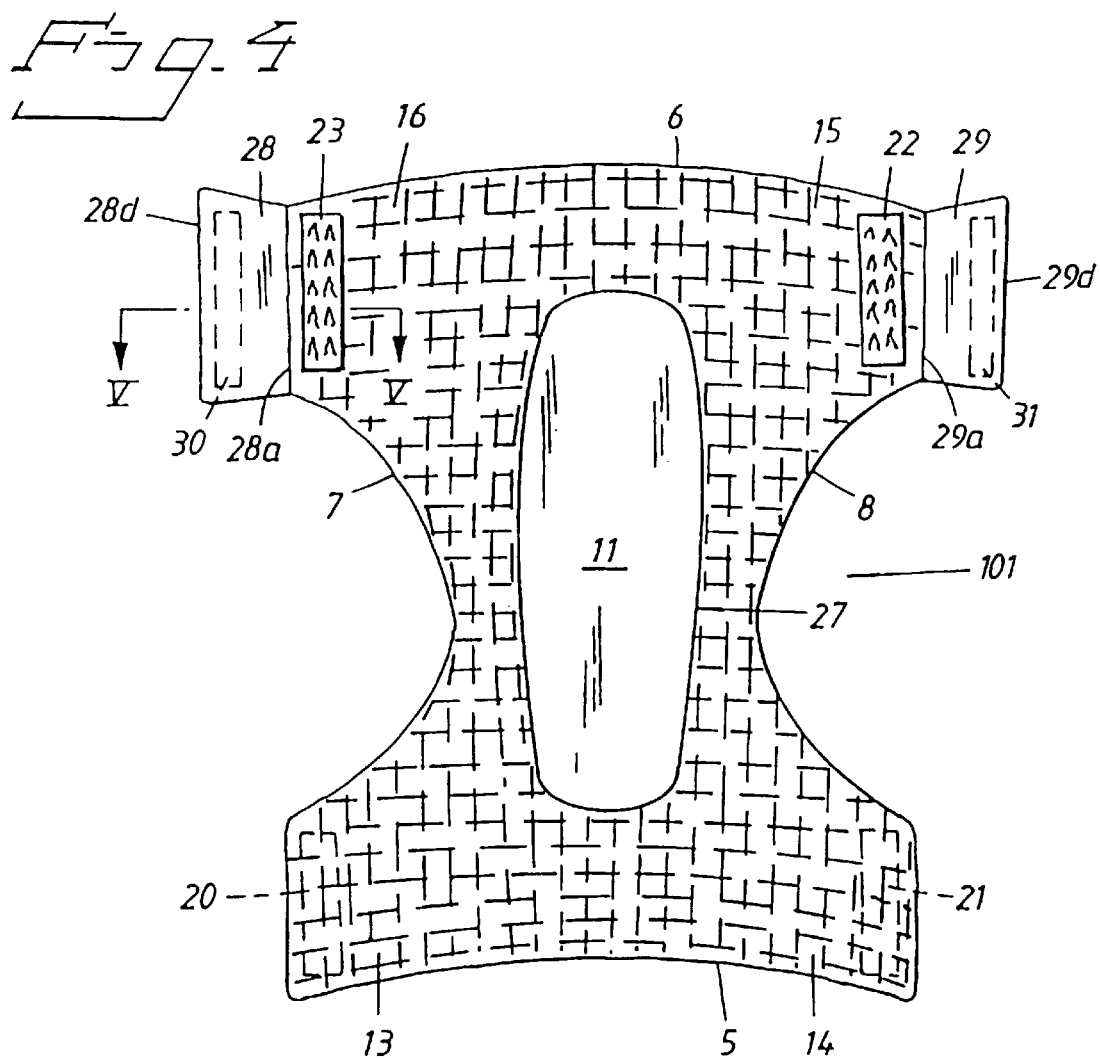
FIG. 4 illustrates from above a diaper according to a second embodiment of the invention.
Figure 5:
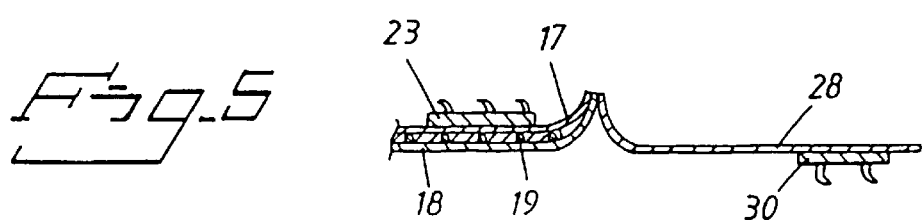
FIG. 5 is a cross-sectional view taken on the line V-V in FIG. 4 and shows gripping means according to the second embodiment of the invention.

The diaper 101 is shown in FIG. 4 with that side thereof which lies proximal to the wearer in use facing towards the viewer. Thus, FIG. 4 shows the whole of elastic pants layer 12 and an elongated opening 27 positioned centrally in the pants layer 12. Urine and faeces are intended to pass through the opening 27 down to the underlying outer material 11 and to the absorbent body 10 located therebeneath.

Instead of a single opening 27, it is conceivable to provide two openings which are mutually separated in the longitudinal direction of the diaper by means of a transverse barrier between the outer material 11 and the pants layer 12. This arrangement will provide mutually separate reception zones between the outer material 11 and the pants layer 12, a front urine receiving zone and a rear faeces receiving zone. Such openings and barriers are described in more detail in our Patent Applications SE 9400916-4 and SE 9400917-2, to which reference is made herewith.

Fastener elements 22, 23 are attached to both rear corner portions 15, 16 of the diaper 101 in the same way as that described with reference to the diaper 1 of the first embodiment illustrated in FIGS. 1–3.

Gripping flaps 28, 29 are provided adjacent the corner portions 15, 15. The gripping flaps 28, 29, however, are of a different kind to the gripping means of the first embodiment.

The gripping flaps 28, 29 are comprised of a gripping means made of a highly pliable material, such as nonwoven material (e.g. a spun-bonded nonwoven or a thermobonded nonwoven), or plastic film (for instance polyethylene) or a combination of these materials. The gripping flaps 28, 29 are elongated in the longitudinal direction of the diaper and are joined along one of their longitudinal edges 28a and 29a respectively along respective diaper side-edges 7, 8.

The grip flaps may be glued or welded to a respective diaper side-edge or affixed thereto in some other conventional manner.

FIG. 4 shows the gripping flaps 28, 29 folded outwards, i.e. with the free longitudinal edge 28d, 29d of respective gripping flaps 28, 29 distanced from respective side-edges 7, 8 of the diaper and with the gripping means orientated in the plane of the diaper 101.

The embodiment illustrated in FIG. 4 also includes extra fastener elements 30, 31 which are attached to the underside of the gripping flaps 28, 29, i.e. to that side of the diaper which in FIG. 4 corresponds to the outside of the corner portion 16. FIG. 5 is a sectioned view taken on the line V—V in FIG. 4 and illustrates the manner in which the grip flap 28 is joined to the diaper side-edge 7 edge-to-edge, and also shows the extra fastener element 30 on the underside of the gripping flap 28, i.e. on the opposite side of the diaper plane relative to the fastener element 23. The purpose of the extra fastener elements is to enable the gripping flaps 28, 29 to be releasably attached to the outside of the corner portions of the diaper when the gripping flaps 28, 29 are not used for their intended purpose.

Figure 6:
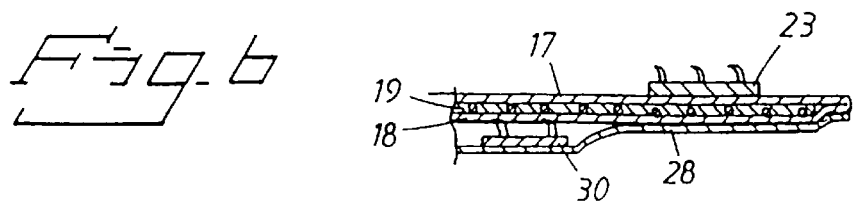
FIG. 6 is a cross-sectional view taken on the same line as FIG. 4 but showing the gripping means in a position different to that shown in FIG. 5.

FIG. 6 shows the gripping flap 28 folded in against the center nonwoven material 18 of the elastic pants layer 12, and shows the extra fastener element 30 in engagement with the outer nonwoven material 18. In the illustrated case, the extra fastener element 30 is a hook-carrying element of a touch and close fastener device, as illustrated schematically by two hooks on a carrier layer. Naturally, the number of hooks will be much greater than the number shown, and said hooks may have a completely different configuration than that illustrated. However, no particular female element is required to connect the hooks, since the pile of the outer nonwoven material functions as loop material into which the hooks can engage. The force required to release the connection between the extra fastener element 30 and the outer nonwoven material 18 need not be particularly great, since the bond thus established fulfils no function with regard to the stability of the diaper on the wearer, but is merely intended to prevent the gripping flaps from hanging down and fluttering along the sides of the diaper. Naturally, if greater forces are desired, separate, knitted loop-carrying material with which the hook-carrying elements are able to bind more strongly may be provided on the outer nonwoven material 18 in the rear corner portions 15, 16 of the diaper. The design of the hook-carrying elements will, of course, also contribute to the fastening forces of the connection and the hook-carrying elements may therefore be chosen freely in accordance with requirements concerning the strength of the bond desired between the gripping flaps 28, 29 and the outer nonwoven material 18 or possibly a separately mounted loop material.

The extra fastener elements 30, 31 may alternatively consist of other mechanical fastener elements, such as buttons and buttonholes, hooks and eyes, press buttons, preferably vacuum-formed press buttons, or different injection-moulded profiles, etc. Naturally, adhesive or cohesive binders may also be used. The number of fastener elements provided on respective gripping flaps 28, 29 may also be greater than the single fastener element shown in FIG. 4, irrespective of whether the fastener devices used are adhesive devices, mechanical devices or some other type of fastener device. For instance, it is conceivable to replace the single elongated extra fastener elements 30, 31 with a row of shorter fastener elements which together extend along the same distance on respective gripping flaps 28, 29 as that shown in FIG. 4.

Naturally, the choice of fastener device will influence the choice of any extra fastener elements on the outer nonwoven material 18 with which the extra fastener elements 30, 31 shall coact. For instance, if an adhesive fastener device is chosen as an extra fastener element 30, 31, a layer treated with release agent may be mounted on the outer nonwoven material in the rear corner portions 15, 16, or some other material layer against which the adhesive fastener element can be released and refastened.

In one variant, the extra fastener element 30, 31 may be placed opposite the fastener element 22, 23 on the inside of the diaper, so that the smallest possible part of the front and rear diaper parts need be used as securing areas. This placement of the extra fastener element would enhance the possibility of making the waist-embracing parts of the diaper elastic over the largest possible part of their surface area.

FIG. 7 illustrates how the second embodiment of the present invention can be used when changing a diaper. The person concerned first releases the gripping flap 29 from its locked use position against the outer nonwoven material. The person concerned then applies a thumb against the gripping flap 29 and the other fingers against the rear side of the gripping flap 29 pressed against the outer nonwoven material essentially along that region which lies centrally behind the fastener device 22. When the fastener elements 21, 22 have mated with one another, they are mutually joined by exerted a light pressure with the outside of the penultimate outer finger joints. The gripping flap 29 is refastened onto the outer nonwoven material with the aid of the extra fastener element. This procedure is then repeated on the other side of the diaper.

It will be understood that further variants of the present invention are conceivable and that the invention is restricted solely by the scope of the following claims.

What is claimed is:

1. An absorbent article comprising:
   a front part which contacts the wearer's stomach during use;
   a rear part which contacts the wearer's buttocks during use;
   a crotch part located between the wearer's thighs during use and extends between said front and rear parts;
   an absorbent body located on the crotch part which is enclosed between a liquid-permeable outer material which lies proximal to wearer's body in use, and a liquid-impermeable barrier layer which lies distal from the wearer's body in use;
   a first and second corner portion in respective front and rear parts of the absorbent article, the first and second corner portions each have a first surface and a second surface which is opposed to the first surface;
   fastener elements disposed on the first surface of the respective first and second corner portions of the rear part of said absorbent article; and
   gripping means provided on the second surface of the first and second corner portions of the rear part of said absorbent article.

2. An absorbent article according to claim 1, wherein the gripping means is comprised of a pocket, a flap or a loop connected to the outside of the first corner portion and the second corner portion of the rear part.

3. An absorbent article according to claim 2, wherein the gripping means is comprised of a part of the first corner and second corner portion of the rear part that is folded over onto itself in a transverse direction of the article to form a folded-over part, wherein the folded-over part is joined to an outer portion of remaining parts of the first corner portion and second corner portion of the rear part along their transverse edges, thus forming a pocket.

4. An absorbent article according to claim 2, wherein said gripping means is elongated and has a longitudinally extending side-edge which extends generally parallel with that edge of respective first corner portion and second corner portion of the rear part which extend generally in a longitudinal direction of the article, two transverse end-edges which are generally orientated in a transverse direction of the article, and a curved longitudinally extending side-edge; and in that the gripping means is joined to the first corner portion and second corner portion of the rear part along at least one of its side edges.

5. An absorbent article according to claim 2, wherein the gripping means are elongated and generally rectangular in shape and are disposed with their longest sides generally parallel with an edge of the respective first corner portion and second corner portion of the rear part which extend generally in a longitudinal direction of the article; and in that the gripping means is joined to the first corner portion and second corner portion of the rear part along at least one of its edges.

6. An absorbent article according to claim 2, wherein said gripping means is joined to the first corner portion and second corner portion of the rear part along three of its edges; and in that a free edge is the edge of the gripping means that is disposed nearest a longitudinally extending contemplated article center line, whereby the gripping means forms a pocket on the outside of respective first corner portion and second corner portion of the rear part.

7. An absorbent article according to claim 4, wherein said gripping means is joined along two opposing edges disposed generally transversely to the longitudinal direction of the article, whereby the gripping means forms a loop on the outside of respective first corner portion and second corner portion of the rear part.

8. An absorbent article according to claim 4, wherein the first corner portion and second corner portion of the rear part have side-edge and said gripping means is joined along one single edge, edge-to-edge, with the side-edge of respective first corner portion and second corner portion of the rear part that extends generally in the longitudinal direction of the article from a waist end-edge to the crotch part.

9. An absorbent article according to claim 8, wherein the gripping means is provided with extra fastener elements for creating a releasable and reclosable connection with the outside of the first corner portion and second corner portion of the rear part, thereby enabling the gripping means to be released from the outside of the first corner portion and second corner portion of the rear part and thereafter reused to close the fastener elements on the first corner portion and second corner portion of the front part of the article with the fastener elements on the first corner portion and second corner portion of the rear part of said article therewith to form a pants-like garment having a waist opening and two leg openings, whereafter the gripping means can be refastened to the outside of the respective first corner portion and the second corner portion of the rear part with aid of extra fastener elements.

10. An absorbent article according to claim 1, wherein respective gripping means are placed essentially immediately above respective fastener elements in respective gripping means use position.

11. An absorbent article according to claim 1, wherein an extension of the gripping means in the longitudinal direction of the article is at least equal to an extension of the fastener elements in a longitudinal direction of the article in respective first corner portion and second corner portion of the rear part.

12. An absorbent article according to claim 1, wherein fastener elements disposed on an outer portion of the first corner portion and second corner portion in the front part of the article.

13. An absorbent article according to claim 2, wherein an area which is joint between the first corner portion and second corner portion of the rear part and the gripping means is a weld joint, a glue joint or a heat seal.

14. An absorbent article according to claim 1, wherein the fastener elements are comprised of a cohesive binder or mechanical fastener elements including hook-carrying elements for coaction with loop-carrying elements, which latter may be comprised of knitted velour material or nonwoven material; press studs, or vacuum-formed press studs.

15. An absorbent article according to claim 9, wherein extra fastener elements are comprised of a cohesive binder or mechanical fastener elements, including hook-carrying elements for coaction with loop-carrying elements, which latter may be comprised of knitted velour material or nonwoven material, press studs, or vacuum-formed press studs.

16. An absorbent article according to claim 1, wherein at least parts of the first corner portion and second corner portion of the rear part exhibit a fibrous outer layer, for instance a nonwoven layer.

17. The absorbent article of claim 1, further comprising fastener elements on the first and second corner portions of the front part of said absorbent article.

18. The absorbent article of claim 1, wherein the second surface of the first and second corner portions of the rear part is an outside surface and the first surface is an inside surface.

19. The absorbent article of claim 17, wherein the second surface of the first and second corner portions of the rear part is an outside surface and the first surface is an inside surface.

20. The absorbent article of claim 1, wherein the fastener elements are disposed on the inside of the first and second corner portions.

21. The absorbent article of claim 1, wherein the gripping means are disposed on the inside of the first and second corner portions.

* * * * *